United States Patent [19]

Wilhelm

[11] 4,228,068
[45] Oct. 14, 1980

[54] PEPTIDE COMPLEXES OF DNA-CONTAINING ORGANISMS

[75] Inventor: Günter R. Wilhelm, Dreieich, Fed. Rep. of Germany

[73] Assignee: R & Z Vermogensverwaltungsgesellschaft mbH, Krefeld, Fed. Rep. of Germany

[21] Appl. No.: 897,549

[22] Filed: Apr. 18, 1978

[30] Foreign Application Priority Data

Apr. 20, 1977 [DE] Fed. Rep. of Germany ....... 2717475
Apr. 20, 1977 [DE] Fed. Rep. of Germany ....... 2717476
Nov. 5, 1977 [DE] Fed. Rep. of Germany ....... 2749554

[51] Int. Cl.$^2$ .................. C07G 7/00; A61K 39/00
[52] U.S. Cl. ................................. 260/112 R; 424/88
[58] Field of Search ................. 260/112 R; 424/88

[56] References Cited

U.S. PATENT DOCUMENTS

| | | | |
|---|---|---|---|
| 2,741,653 | 4/1956 | Kutsy | 260/112 R |
| 3,862,109 | 1/1975 | Mitsuda et al. | 260/112 R |
| 3,887,431 | 6/1975 | Robbins et al. | 260/112 R X |
| 3,991,215 | 11/1976 | Robbins | 260/112 R X |
| 3,996,104 | 12/1976 | Lindblom et al. | 260/112 R X |
| 4,007,088 | 2/1977 | Fencl et al. | 260/112 R X |

FOREIGN PATENT DOCUMENTS

473720  9/1975  U.S.S.R. ........................... 260/112 R

OTHER PUBLICATIONS

Cavalieri et al., *Proc. Nat. Acad. Sci.*, vol. 67, No. 2, (1970), pp. 807–812.

*Primary Examiner*—Walter C. Danison
*Attorney, Agent, or Firm*—Cushman, Darby & Cushman

[57] ABSTRACT

DNA peptide complexes are prepared from organisms containing DNA to produce specific peptide complexes in a substantially pure state and useful for diagnostic, therapeutic and prophylactic purposes. The complexes can be prepared from bacteria, fungi, plants, human or animal tissue by homogination, centrification, absorption on DEAE cellulose, serial elution of the cellulose followed by dialysis and collection.

3 Claims, No Drawings

PEPTIDE COMPLEXES OF DNA-CONTAINING ORGANISMS

The present invention relates to peptide complexes of DNA-containing organisms.

It is known that peptides of most varied compositon, alone or in combination with polysaccharides or lipids, may show specific antigen determinants. These substances are effective in part as haptenes only, and in part as immunogens. Numerous studies have been performed with the aim of isolating antigens from the most varied organisms, which antigens might be used for diagnostic, therapeutic or prophylactic purposes in human or veterinary medicine. The antigens presently available in human and veterinary medicine are mostly mixtures of in part active and in part inactive proteins, polysaccharides, lipids and nucleic acids. As an example for the diagnostic utilization of compositions of this type, reference may be made to the purified tuberculin as used for the diagnosis of tuberculosis. In the prophylactic use for providing protection by inoculation against bacterial or fungus infections, compositions of this kind, such as, for instance, the purified tuberculin, are not satisfactory. This fact makes it necessary to administer intact, live or dissolved microorganisms, as is done in the inoculation against tuberculosis, pertussis or salmonella. These methods involve a not unsubstantial danger to the patients.

Accordingly, it is the object of the present invention to provide antigens which can be accurately defined in chemical respects, which are substantially pure and which may be used at the same time for diagnostic, therapeutic and prophylactic purposes.

In accordance with the invention, it has become possible to isolate from any DNA-containing organism an antigen group having specific antigen determinants each for the organism from which it is isolated.

These antigen groups comprise peptide complexes of DNA-containing organisms showing the following characteristics:

(a) a molecular weight of less than 5,000;

(b) forming a ribonucleic acid compound having an average molecular weight of from about 9,000 to 20,000 which forms a singular, uniform band in the gel electrophoresis and acetate sheet electrophoresis;

(c) preferably intracellular occurence;

(d) a calcium content;

(e) a precipitation reaction with terbium-III ions;

(f) an extremely good solubility in water;

(g) an average content of asparatic acid and glutamic acid of about 30 mole percent (based upon the total amino acid content);

(h) a molar ratio (asparatic acid+glutamic acid) to (lysine+arginine) of greater than 1;

(i) an origin-specific amino acid composition;

(k) antigenous activity, and (l) capability of increasing resistance.

Peptide complexes of the type according to the present invention are prepared from a known per se ribonucleoprotein fraction (RNP). The RNP is obtained as follows (compare Wilhelm G. Sellier, "Biophysik" 1973, pages 69 to 78 and 257 to 265):

(a) The organisms or parts thereof are homogenized, in a natural or denaturated state, in 0.2 M phosphate buffer at a pH of 7.2;

(b) the homogenate is centrifuged;

(c) the supernatant is stirred with DEAE cellulose loaded with phosphate buffer, and charged into a column;

(d) the loaded DEAE cellulose is eluted with 0.2 M phosphate buffer until the absorption of the eluate at 280 nm is below 0.1; then, it is further eluted with 0.1 M acetic acid-acetate solution (pH 3.2) until the absorption of the eluate at 280 nm is again below 0.1; thereafter, an eluation is effected with a 3 percent by weight NaCl-containing 0.1 M acetic acid-solution (pH 3.2), and the ribonucleoprotein fraction (RNP) appearing with the NaCl front in the eluate is collected, dialyzed against water, condensed and lyophilized.

In accordance with the present invention, the peptide complexes, inter alia, may be prepared in accordance with three different methods. The indicated modes of obtaining these complexes are not restrictive. Depending on circumstances, it is also possible, after a respective sequential analysis, to obtain the peptide complexes by a synthetic method, as is known from the amino acid art.

Therefore, only three possible types of methods are characterized below:

(I) The lyophilized RNP dissolved in water is blended with phenol, heated to about 95° to 100° C., centrifuged to separate the phases upon cooling, the phenol phase is mixed with water and then repeatedly washed out with ether. The aqueous residue is lyophilized.

(II) The RNP dissolved in water is subjected to a high-voltage electrophoresis, and the peptide complex is isolated in the usual manner.

(III) The peptide complex is isolated from the RNP dissolved in water by thin film chromatography.

Furthermore, the present invention relates to a medicament or drug containing a peptide complex according to the invention in a customary pharmaceutical carrier or substrate, optionally in combination with customary pharmaceutical additives.

The peptide complexes according to the invention may be obtained by the processes described below. The parts specified in the Examples, unless specifically designated as parts by volume, refer to parts by weight.

EXAMPLE 1

Native or denaturated bacteria, fungi, plants, human or animal tissue are homogenized in an Ultra-Turrax and Potter homogenisator, in 0.2 M phosphate buffer at a pH of 7.2. The homogenate is centrifuged until the supernatant is clear. The supernatant is stirred with DEAE cellulose loaded with phosphate buffer for 30 minutes. The DEAE cellulose is washed from three to five times with 0.2 M phosphate buffer, and the washing solution is discarded each time. Then, the loaded DEAE cellulose is charged into a column and washed with the above phosphate buffer until the extinction or absorption at 280 nm is decreased below 0.1. Thereupon, further washing is effected with 0.1 M acetic acid-acetate solution (pH 3.2) until the extinction is lowered to below 0.1. Then, 3% of NaCl ia added to the acetic acid solution, and the ribonucleoprotein fraction appearing with the NaCl front in the eluate is collected. Upon dialyzing against distilled water, the ribonucleoprotein fraction is concentrated and lyophilized. The yield varies. It amounts to about 30 mg for 30 grams of bacteria and fungi, while the yield depends on the kind of plant, animal and human tissue being treated.

The ribonucleoprotein (RNP) is thereafter subjected to a modified phenol extraction according to Westphal (Z.Naturforschung 7 b (1952), p. 148 to 155). This process is carried out as follows: The RNP is dissolved in aqua dest. (about 1.5 ml of H₂O per 10 mg of RNP). One half of the quantity of liquefied phenol p. a. is added to this solution (10 ml of aqua dest.+5 ml of phenol). This mixture is heated, with agitation, to from 95° to 100° C. for about 10 minutes. Then, the mixture is cooled to about 2° to 3° C. The mixture is centrifuged until exact separation of the phases is reached. The H₂O phase contains RNA+fractions+amino acids. The phenol phase saturated with H₂O contains the peptide complex. The phenol phase is mixed with one half of the volume of fresh aqua dest. and shaken out with a threefold to fivefold excess of ether. This procedure is repeated two times in its full sequence. Following the phenol elimination, the aqueous residue which now contains the purified peptide, is optionally pressed through a sterile filter (Millipore) and freeze dried. Yield of the extraction is about 1 to 1.5% of peptide complex, based upon RNP. The ether phase is discarded upon separation in the shaking bulb.

EXAMPLE 2

The peptide complexes according to the invention may be obtained from the ribonucleoprotein (RNP) prepared, for instance, according to Example 1, also by high-voltage electrophoresis.

To this end, the RNP solution is applied to Whatman No. 1 electrophoresis paper. The electrophoresis is performed in 0.1 M acetic acid-pyridine buffer (pH 5.7; 50 V/cm) for a period of 30 minutes. Upon the dyeing of the margins, the bands adapted to be dyed with amido black and ninhydrine are out and eluted with distilled water.

The thus eluted peptide complexes are readily soluble in distilled water and physiological saline solutions. The peptide complexes may be filtered through Sephadex-filters and bacteria retaining filters.

EXAMPLE 3

Preparation can also be accomplished by preparative thin film chromatography. The RNP solution is applied to a preparative silica gel plate and subjected to increasing chromotography in a mixture of chloroform, methanol and acetic acid (2:2:1) for a period of from about 1 to 2 hours. Upon drying the plate, an marginal strip is dyed with ninhydrin, and a second separated strip is dyed with amido black. Each of the desired peptide complex is each eluted from the respective dyed band and recovered from the eluate.

Peptide complexes obtained in accordance with the above Preparation Examples 1 to 3 are specific according to their origin. Depending on the organism from which these complexes were prepared, they differ in the composition of amino acids. The following Table summarizes the approximate amino acid analyses of some peptide complexes according to the invention as obtained from various organisms:

|  | Myco-bact. tbc. | B per-tussis | E. coli | S. typhi | Str. pyog. | Humane lymph-ocytes |
|---|---|---|---|---|---|---|
| Asparatic acid | 0,035 | 0,067 | 0,038 | 0,0049 | 0,042 | 0,025 |
| Threonine | 0,013 | 0,025 | 0,019 | 0,0026 | 0,024 | 0,010 |
| Serine | 0,017 | 0,031 | 0,043 | 0,0090 | 0,020 | 0,017 |
| Glutamic acid | 0,035 | 0,074 | 0,092 | 0,0114 | 0,076 | 0,025 |
| Proline | 0,018 | 0,024 | — | — | — | 0,017 |
| Glycine | 0,032 | 0,082 | 0,049 | 0,0540 | 0,025 | 0,020 |
| Alanine | 0,030 | 0,074 | 0,036 | 0,0043 | 0,035 | 0,015 |
| Valine | 0,011 | 0,040 | 0,023 | — | 0,024 | 0,015 |
| Isoleucine | — | — | 0,021 | — | 0,019 | — |
| Leucine | 0,016 | 0,029 | 0,018 | — | 0,026 | 0,025 |
| Phenylalanine | — | — | — | — | — | 0,010 |
| Lysine | — | 0,026 | 0,016 | — | 0,024 | 0,010 |
| Arginine | — | — | 0,014 | — | — | 0,015 |

The above analysis would result in approximately the following amino acid distribution in the peptide complexes:

|  | Myco-bact. tbc. | B. per-tussis | E. coli | S. typhi | Str. pyog. | Humane lymph-ocytes |
|---|---|---|---|---|---|---|
| Asparatic acid | 2 | 3 | 2 | 1 bzw. 2 | 2 | 3 |
| Threonine | 1 | 1 | 1 | 1 ? | 1 | 1 | 1 |
| Serine | 1 | 1 | 2 | 2 bzw. 3 | 1 | 2 |
| Glutamic acid | 2 | 3 | 5 | 2 bzw. 4 | 4 | 3 |
| Proline | 1 | 1 | 0 | 0 | 0 | 0 | 2 |
| Glycine | 2 | 3 | 2–3 | 11 bzw. 21 | 1 | 2–3 |
| Alanine | 2 | 3 | 2 | 1 bzw. 1–2 | 2 | 2 |
| Valine | 1? | 1–2 | 1 | 0 | 0 | 1 | 2 |
| Isoleucine | 0 | 0 | 1 | 0 | 0 | 1 | 0 |
| Leucine | 1 | 1 | 1 | 0 | 0 | 1 | 2 |
| Phenylalanine | 0 | 0 | 0 | 0 | 0 | 0 | 1 |
| Lysine | 0 | 1 | 1 | 0 | 0 | 1 | 1 |
| Arginin | 0 | 0 | 1? | 0 | 0 | 0 | 2 |

The peptide complexes isolated from the various organisms in the manner as disclosed in the above Examples may be utilized, for example, for producing specific antibodies, for the demonstration of a specific, retarded immunity and for the increase transfer of a specific, retarded immunity or transfer factor characteristic. This may be explained by the following examples demonstrating specific uses of the materials:

EXAMPLE A

For the generation of specific antibodies, the peptide complexes that were isolated—as disclosed above—from various organisms are administered to rabbits. To this end, 10 to 100 μg (micrograms) of peptide complex are dissolved in 0.9% NaCl and emulgated in the ratio of 1:1 with Freund's adjuvant. This dose is injected into the feet of the animals in four equal quantities. Two weeks later, 10 μg of peptide complex are administered intraveneously for booster purposes. The serum of the animals is examined for the formation of antibodies by the Ouchterlony test. The boostering is repeated in periods of eight days until readily noticeable Ouchterlony reactions are observed. In most cases, one to three booster injections are sufficient to this end. In the Ouchterlony test, the antibodies formed are examined for specificity. The examination shows that the peptide complexes isolated from various organisms generate specific antibodies. In the case of peptide complexes obtained from bacteria, for instance, it is striking that there does not exist any type or group specificity.

EXAMPLE B

From thermally mortified tuberculosis bacteria (Mycobacterium tuberculosis, typus humanus or bovinus), the peptide complex according to the invention is prepared in accordance with the process of Examples 1 to 3. This complex is readily soluble in water and in saline solutions isoosmotic to blood serum. The complex is insoluble in organic solvents, such as alcohol, ether, chloroform, and it is practically free of nucleic acids, polysaccharides and lipids.

On the basis of the amino acid composition according to Table 1, a molecular weight of about 1,200 is calculated. A measurement in the mass spectrograph shows a molecular peak at 1,152. Other characteristics are:

The peptide complex may be filtered through a UM2 membrane supplied by Amicon.

The peptide complex contains calcium in an amount of about 1 mole per mole of peptide. The calcium is relatively strongly bonded, and it is probably present in the form of a complex bond.

The peptide complex migrates uniformly with thin film chromatography with chloroform, methanol and ammonia (2:2:1) as a carrier.

The antigenity of the complex is not affected even by heating to 100° C. for several hours in aqueous solutions and at neutral pH values.

The antigenity of the complex is not substantially affected by heating to 100° C. in 1 n acetic acid for a period of 2 hours.

The complex is precipitated partially by the addition of terbium-III-chloride solutions in highly diluted concentrations. Thus, the complex is rendered less soluble in aqueous solutions.

The peptide complex is standardized against purified tuberculin in guinea-pigs. About one ng corresponds to one tuberculin unit (purified tuberculin of Farbwerke Hoechst AG).

For the intracutaneous test, the peptide complex is dissolved in 0.9% NaCl solution. Heating to 100° C. does not adversely affect the activity. The dissolved peptide complex is stable for several months, without loosing its activity. The test is performed with concentrations graduated by tenth powers. 0.1 ml are each injected strictly intracutaneously. The readings are taken after 24, 48 and 72 hours, by measuring the infiltrate.

By means of tests with 1 ng and 10 ng, the possibility of the existence of active tuberculosis (extrapulmonary and pulmonary forms) of the infant may be detected with a high degree of certainty within a period of 48 hours. With 0.1 ng and 1 ng, the potential existence of extrapulmonary tuberculosis in infants and adults can be ascertained with a high degree of certainty within a period of 48 hours. Infants inoculated with BCG remain negative to a high percentage when tested with 1 ng. A great selectivity between BCG-inoculated persons and and persons actually affected by tuberculosis can be observed. Small infiltrates can already be considered as specific. This fact could be proven histologically with an infiltrate having a diameter of 3mm and initiated with 0.1ng. Non-infected persons do not show any reaction. Nonspecific reactions could not be observed.

Adults with tertiary pulmonary tuberculosis show, in later stages, weaker reactions as compared to patients in less advanced stages of disease. Patients with tuberculous pleuritis exhibit weaker reactions than patients with pulmonary tuberculosis without pleuritis. The reactions initiated by the peptide complex with respect to the dependence of concentration and the extent of reaction are not identical with the reactions caused by purified tuberculin.

Advantages of the testing with the peptide complex are as follows:

1. More rapid progress of the retarded immune reaction; in this way, the reading is at an optimum afer 24 hours.

2. A test with 1 ng of peptide allows in at least 75% of the cases to determine the existence of an active tuberculosis in infants.

3. Two tests with 1 ng and 10 ng of peptide provide a high degree of certainty of recognizing a potential tuberculous infection in the infant, independently of the type of tuberculosis.

4. The high sensitivity of patients affected by extrapulmonary types of tuberculosis to the peptide permits a quick and positive diagnosis of this kind of tuberculosis to be made.

5. The high degree of selectivity between BCG-inoculated persons and diseased persons saves unnecessary expenditure in diagnosis, particularly X-ray examinations.

6. No unspecific side reactions, except for a temporary slight reddening lasting for up to 1 hour after the injection, could be observed.

For the above-discussed reasons, the peptide is superior to the tuberculin, even in the purified form of the latter. As a singular, highly potent antigen, the peptide meets every requirement that must be imposed on a test material for the recognition of a tuberculous infection. This material may be considered as the long sought for, plain principle of the tuberculosis Test materials.

EXAMPLE C

Determination of the stimulation of lymphocytes in the lymphocytetransformation test according to Hartzman et al. (Transplantation 11 (1971), p. 268 to 273). In the lymphocyte transformation test, the peptide complex prepared in accordance with one of Examples 1 to 3 brings about a dose-dependent stimulation of the lymphocytes of tuberculin-positive, naturally infected persons with a range of doses of from 1 $\mu$g to 10 pico-grams oligopeptide complex per culture. Lymphocytes of tuberculin-negative persons are not stimulated. An unspecific basis stimulation as is caused by purified tuberculin (Proc. Nat. Acad, Sci., USA, Vol. 71 (1974), p. 1178 to 1182), cannot be proven. In contrast with the lymphocytes of naturally infected persons, lymphocytes of BCD-inoculated persons could not be stimulated to any measurable degree. Lymphocytes of persons suffering from tuberculous pleuritis could not be stimulated to any measurable degree, either.

EXAMPLE D

Serum samples of persons affected by leprosy or tuberculosis or healthy persons showing a positive reaction to tuberculin, as well as of persons showing a negative reaction to tuberculin, were examined in the Micro-Ouchterlony test for humoral antibodies against the peptide complex isolated from Mycobacterium tuberculosis. No reactions were found in healthy persons reacting negatively and positively to tuberculin. In the case of persons infected with tuberculosis, only sporadic precipitation reactions occured. These sera were obtained exclusively from patients suffering from advanced tertiary pulmonary tuberculosis. In the case of lepers with a lepromatous form, of course, remarkably strong precipitation reactions occured, while lepers with a tuberculous form of disease exhibited only weak reactions or no reaction.

Nevertheless, according to the above Examples B to D exact in vitro determinations of the retarded immunity in the case of tuberculosis and leprosy are practical. This fact represents an immense advance in the art. The peptide complex may be employed for increasing the resistance against infection by Mycobacterium tuberculosis. Due to the common antigen determinant with Mycobacterium leprae, the oligopeptide complex according to the invention may be utilized for increasing the resistance to infection by *Mycobacterium leprae*.

EXAMPLE E

Pertussis (whopping-cough) has been in view of lethality and complications, one of the most dangerous infectious diseases of infancy until the present time. Particular danger exists for children in their first six to eight months of life. The inoculation with intact *Bordetella pertussis* germs is more of a risk than many other types of inoculation. It is thus necessary to administer with the resistance increasing factors, the entirety of the substances present in the germs, namely substances which are in part toxic in nature and which contain a number of antigens that do not show any relation to the resistance, but that result in no undesired reactions of the organism.

Now, it has been found that these disadvantages can be avoided and an increase in resistance can be obtained by employing for th inoculation a small peptide complex according to the invention recovered from *Bordetella pertussis* germs.

The isolation of the present peptide complex from *Bordetella pertussis* germs is effected by homogenizing the thermally (deactivated) *Bordetella pertussis* germs and separating as far as possible the thus obtained preparation from the remainder of its constituents by centrifuging, filtering by means of suitable filters or sedimentation. Thereupon, the liquid phase obtained may be subjected to a separation method of the kind described in Examples 1 to 3. From 30 g of lyphilized, thermally deactivated bacteria, one obtains about 30 mg of peptide complex substance in a lyophilized form.

The amino acid composition of the peptide complex prepared is apparent from Table 1. On this basis, the probable molecular weight may be calculated to be 1,760 (with 1 valine), or 1,880 (with 2 valines). Other characteristics are as follows:

The peptide is adapted to be filtered through a UM2 membrane available from the Amicon Company.

The peptide contains calcium in an amount of about 1 mole per mole of peptide. The calcium is relatively strongly bonded and probably present in a complex bond.

The peptide proves to be a homogenous substance with the carrier medium chloroform, methanol, ammonia (2:2:1) in thin film chromatography.

The peptide is stable when heated to 100° C. in aqueous solutions.

The peptide is precipitated with a high degree of dilution by the addition of a terbium-III-chloride solution. Hereby, it is rendered insoluble in aqueous solutions.

The peptide is practically free of nucleic acids, polysaccharides and lipids.

The peptide is readily soluble in water and in saline solutions is isoosmotic against blood serum. It is insoluble in organic solvents, such as alcohol, ether or chloroform.

The peptide complex isolated from *Bordetella pertussis* bacteria was dissolved in 0.9% NaCl solution, and the respective concentration used for inoculation was mixed with complete Freund's adjuvant in a ratio of 1:1.

White mice of a weight of from 17 to 22 grams were given an intramuscular injection of the peptide complex (e.g., 1 µg per mouse, 0.1 µg per mouse, 0.01 µg per mouse). After a period of 14 days, an intracerebral challenge infection with *Bordetella pertussis* germs was carried out in accordance with the instructions of the "Furopäsches Arzneibuch für die Impfstoffprüfung". As appears from the mortality curve, an increase in resistance depending on the dose was obtained. With 1 µg/mouse of peptide complex of *Bordetella pertusses*, the resistance increasing effect is already excellent. This corresponds to the protective dose of 0.1 IE of the commercially available pertussis vaccine containing mortified bacteria, while the peptide complex does not exhibit the above-discussed disadvantages of this vaccine.

The novel type of inoculation against infection by *Bordetella pertussis* means a great advance in the art. The dangers involved with the conventional vaccine are avoided. Inoculation may be practiced in early infancy, i.e. in the period of maximum exposure. The novel vaccine is extremely stable to temperature effects and is storable for a long period of time (months and years). It represents a resistance increasing principle without any harmful accompanying substances. Thus, the novel vaccine fulfills every criterion of an ideal vaccine against bacterial infection.

By means of the method according to Examples 1 to 3, peptide complexes may be isolated from many other species of bacteria and other DNA-containing organisms, which complexes are shown to be highly potent antigens being specific for the respective organism. The peptides are each characterized by an unique amino acid composition. It is herein apparent that the increase or improvement of resistance which can be noted in the case of pertussis and tuberculosis (compare Examples B to E) indicates only one example for the specifically resistance-increasing property of the specific peptides of this group.

EXAMPLE F

The specific peptide complex isolated from streptococcus is dissolved in 0,9% NaCl. With an intracutaneous injection of from 10 to 100 ng of peptide complex, retarded skin reactions occur predominantly in patients with rheumatic fever and acute, diffuse glomerulonephritis, which reactions in their manner of occurence and intensity differ from the reactions in healthy control persons.

EXAMPLE G

With the specific peptide complex isolated from streptococcus (*Streptococcus pyogenus*), positive reactions with the serum of patients suffering from rheumatic fever and acute diffuse glomerulonephritis are observed in the Ouchterlony test. The antibody level may be quantiatively determined by means of the Laser Nephelometer available from Behringwerke AG (Marburg/Germany). To this end, varying amounts of the peptide complex, e.g. 10 ng, 100 ng, 1 μg) are added to 200 μl (microliter) of serum.

EXAMPLE H

The specific peptide complex isolated from Escherichia coli is dissolved in 0.9% NaCl. In the Ouchterlony test, positive reactions are observed in the serum of patients affected by Colitis ulcerosa. In unaffected persons (e.g. blood donor sera), weak reactions can be found only in some few cases. The quantitative determination of the antibody level may be performed by using the Laser Nephelometer (Behring). To this end, varying amounts of the peptide complex (e.g. 10 ng, 100 ng, 1 microgram) are added to 200 microliter of serum.

EXAMPLE I

The specific peptide complex isolated from Salmonella typhi bacteria is dissolved in 0.9% NaCl. In the Ouchterlony test, positive reactions can be observed in the serum of patients who have been diseased with typhus or who have been suffering from typhus for from two to three weeks. The quantitative determination of the antibody level may be effected e.g. with the Laser Nephelometer. To this end, varying amounts of the peptide complex (e.g. 10 ng., 100 ng, 1 microgram) are added to 200 microliter of serum.

EXAMPLE K

The specific peptide complex isolated from *Candida albicans* fungi is dissolved in 0.9% NaCl. In the Ouchterlony test, positive reactions are found to take place in the serum of patients who are, or have been, diseased with *Candida albicans* infection. The antibody level may be quantitatively determined e.g. by means of the Laser Nephelometer. To this end, varying amounts of the peptide complex (e.g. 10 ng,,100 ng, 1 μg) are added to 200 μl of serum.

EXAMPLE L

From synovia obtained by surgical operation from the inflamed joints of patients diseased with rheumatcidal arthritis, the peptide complex is prepared in the manner specified in Examples 1 to 3. The peptide complex is dissolved in 0.9 NaCl. In the Ouchterlony test, positive reactions are observed in the serum of persons affected by rheumatoidal arthritis. The quantitative determination of the antibody level may be performed e.g. with the Laser Nephelometer. To this end, varying amounts of the peptide complex (e.g. 10 ng, 100 ng, 1 microgram) are added to 200 microliter of serum.

EXAMPLE M

From blasto cells of patients affected by an acute lymphatic leukaemia, a peptide complex is prepared in the manner specified in Examples 1 to 3. As a control, a peptide complex is recovered also from normal lymphocytes. These two peptide complexes are dissolved in 0.9% NaCl. 10 ng to 1 μg of both peptide complexes are infused strictly intracutaneously in 0.1 ml of solution. Administration takes place at the inner side of the forearms, with the peptide complex of blasto cells being applied to each right arm and the peptide complex of normal lymphocytes being applied to each left arm. The occurence of a typical, retarded reaction is considered as a positive reaction. Whereas positive reactions cannot be observed to take place in the case of the peptide complex obtained from normal lymphocytes, the complex isolated from blasto-cells induced retarded reactions in part of the test persons. The retarded reactions show a characteristic dispersion, and these reactions occur with high frequency in persons being in contact with patients affected by acute lymphatic leukaemia.

EXAMPLE N

When the present peptide complex according to Examples 1 to 3 is obtained from lymphocytes of a human organism exhibiting a retarded immunity against a specific antigen, e.g. tuberculin, and this peptide complex is injected into another person not showing any retarded immunity against said antigen, then the abovementioned peptide complex released a retarded immunity in the previously not immune person, with such immunity being directed against the person not abovementioned antigen. Accordingly, the peptide complex recovered from lymphocytes shows transfer factor properties for the retarded immunity.

EXAMPLE O

The specific peptide complexes are coupled to $^{125}I$ in accordance with the method of Hunter (Hunter, W. M., Radioimmunoassay in: Handbook of Experimental Immunology, Vol. 1: Immunochemistry, Chapter 17, Sec. Edition, Blackwell Scientific Publications, Oxford-London-Edinbourgh-Melbourne, 1973). With the radioactively marked peptide complexes, radioimmunoassays specific to the respective peptide complex employed are performed.

What I claim is:

1. The peptide complex, obtained from desoxyribonucleic acid-containing organisms, wherein
   (a) said organisms and parts or constituents thereof are homogenized in a native or denatured state in 0.2 M phosphate buffer (pH 7.2);
   (b) said homogenate is centrifuged;
   (c) the supernatant is stirred with phosphate buffer-loaded DEAE cellulose and charged into a column;
   (d) the loaded DEAE cellulose is eluted with 0.2 molar phosphate buffer until the absorption of the eluate at 280 nm is below 0.1, and thereafter further eluted with 0.1 M acetic acid-acetate solution (pH 3.2) until the absorption of the eluate at 280 nm is again below 0.1, thereupon eluted with a 3% NaCl containing 0.1 M acetic acid (pH 3.2) and the ribonucleic acid fraction (RNP) appearing in the eluate with the NaCl front is collected, dialyzed against water, concentrated and lyophilized, characterized in that
   I. the lyophilized RNP dissolved in water is mixed with phenol, heated to about 95° to 100° C. and, upon cooling, centrifuged until the phases are separated, the phenol phase is mixed with water and then repeatedly shaked out with ether, and the aqueous residue is lyophilized; or
   II. the RNP dissolved in water is subjected to high-voltage electrophoresis, and the peptide complex is isolated; or
   III. the peptide complex is isolated from the RNP dissolved in water, by thin film chromatography.

2. The peptide complex according to claim 1, wherein the complex is obtained from organisms of the species *Mycobacterium tuberculosis* or *leprae*, or from *Bordetella pertussis, Escherichia coli, Salmonella typhi, Streptococcus pyogenus* or *Candida albicans.*

3. The peptide complex according to claim 1, wherein the complex is obtained from blasto cells of human patients affected by acute lymphatic disease, of synovia of the inflamed joint or of lymphocytes.

* * * * *